(12) United States Patent
Batchelor et al.

(10) Patent No.: US 11,129,633 B2
(45) Date of Patent: Sep. 28, 2021

(54) MEDICAL DEVICE INTERFACE

(71) Applicant: GYRUS ACMI, INC., Southborough, MA (US)

(72) Inventors: Kester J. Batchelor, Mound, MN (US); Nikhil Murdeshwar, Maple Grove, MN (US); William Butler, Minneapolis, MN (US)

(73) Assignee: Gyrus Acmi, Inc., Westborough, MA (US)

(*) Notice: Subject to any disclaimer, the term of this patent is extended or adjusted under 35 U.S.C. 154(b) by 104 days.

(21) Appl. No.: 16/310,516

(22) PCT Filed: Jun. 24, 2016

(86) PCT No.: PCT/US2016/039200
§ 371 (c)(1),
(2) Date: Dec. 17, 2018

(87) PCT Pub. No.: WO2017/222549
PCT Pub. Date: Dec. 28, 2017

(65) Prior Publication Data
US 2019/0336154 A1 Nov. 7, 2019

(51) Int. Cl.
A61B 17/28 (2006.01)
A61B 17/285 (2006.01)
(Continued)

(52) U.S. Cl.
CPC .......... A61B 17/285 (2013.01); A61B 17/30 (2013.01); A61B 17/3213 (2013.01);
(Continued)

(58) Field of Classification Search
CPC ... A61B 17/285; A61B 17/30; A61B 17/3213; A61B 18/1442; A61B 2017/0046;
(Continued)

(56) References Cited

U.S. PATENT DOCUMENTS 4,375,218 A * 3/1983 DiGeronimo .......... A61B 17/30
606/52
4,640,279 A 2/1987 Beard
(Continued)

FOREIGN PATENT DOCUMENTS

JP 2000/102545 A 4/2000
WO 1995/31144 A2 11/1995
(Continued)

OTHER PUBLICATIONS

International Search Report for Application No. PCT/US2016/039200 dated Feb. 1, 2017.
(Continued)

Primary Examiner — Erich G Herbermann
(74) Attorney, Agent, or Firm — Schwegman Lundberg & Woessner, P.A.

(57) ABSTRACT

A medical device comprising: (a) an interface including: (i) a first portion including: (1) a body portion connected to N a handle of a scalpel; and (2) a connection adapter; (ii) a second portion; wherein the connection adapter includes an interface portion that is a channel and the second portion includes an interface portion that is a tab that extends into the channel so that the first portion is connected to the second portion or wherein the second portion includes an interface portion that is a channel and the connection adapter includes an interface portion that is a tab that extends into the channel so that the first portion is connected to the second portion.

19 Claims, 9 Drawing Sheets

(51) Int. Cl.
  *A61B 17/30* (2006.01)
  *A61B 17/3213* (2006.01)
  *A61B 18/14* (2006.01)
  *A61B 17/00* (2006.01)
  *A61B 18/00* (2006.01)

(52) U.S. Cl.
  CPC .. *A61B 18/1442* (2013.01); *A61B 2017/0046* (2013.01); *A61B 2018/00178* (2013.01); *A61B 2018/00589* (2013.01); *A61B 2018/1455* (2013.01); *A61B 2018/1462* (2013.01)

(58) Field of Classification Search
  CPC .......... A61B 2018/00178; A61B 2018/00589; A61B 2018/1455; A61B 2018/1462; A61B 17/29; A61B 17/295; A61B 2017/2906; A61B 2017/2926; A61B 2018/1457; A61B 2018/146
  See application file for complete search history.

(56) References Cited

U.S. PATENT DOCUMENTS

| | | | |
|---|---|---|---|
| 4,651,734 A | 3/1987 | Doss et al. | |
| 5,207,696 A | 5/1993 | Matwijcow | |
| 5,569,243 A * | 10/1996 | Kortenbach | .......... A61B 17/29 606/46 |
| 5,891,142 A | 4/1999 | Eggers et al. | |
| 6,929,645 B2 | 8/2005 | Battles et al. | |
| 9,027,254 B1 | 5/2015 | Vodinh | |
| 2008/0243141 A1 | 10/2008 | Privitera et al. | |
| 2014/0276772 A1 | 9/2014 | Batchelor et al. | |
| 2014/0276795 A1 * | 9/2014 | Batchelor | .......... A61B 18/1445 606/42 |

FOREIGN PATENT DOCUMENTS

| | | |
|---|---|---|
| WO | 2015/184424 A1 | 12/2015 |
| WO | WO-2017222549 A1 | 12/2017 |

OTHER PUBLICATIONS

"International Application Serial No. PCT/US2016/039200, International Preliminary Report on Patentability dated Jan. 3, 2019", 8 pgs.

"International Application Serial No. PCT/US2016/039200, Written Opinion dated Feb. 1, 2017", 6 pgs.

* cited by examiner

MEDICAL DEVICE INTERFACE

FIELD

The present teachings generally relate to an interface that connects to one or more and preferably two or more surgical instruments so that a combination of surgical instruments can be used together during a surgical procedure, the interface being especially adapted to introduce a scalpel into forceps or to add forceps arms to a scalpel.

BACKGROUND

Typically, during surgical procedures, surgeons use a cold bladed scalpel to cut and bipolar tweezers to coagulate, hold, and/or move anatomical features of interest. In using both devices the surgeon often makes a cut with a scalpel and then switches to the bipolar forceps to coagulate or perform some other step. Once that step is over the surgeon may have to switch back to the scalpel and repeat the steps of switching multiple times. The time needed to switch between the two devices can be bothersome to the user, result in a temporary loss of concentration, a temporary loss of footswitches, temporary loss of hand controls, require manipulation of the devices upon each switch, loss of field of view during switching, or a combination thereof. Thus, it would be desirable to have a device that includes a cold bladed scalpel into bipolar forceps so that both can be used without switching between the two different devices. Additionally, surgeons may desire other functionality to be added to the surgical device at times or removed from the surgical device at times, however, most surgical devices do not include ports that allow for adding or subtracting functionality or surgical devices.

Examples of some surgical instruments may be found in U.S. Pat. Nos. 4,375,218; 4,640,279; 4,651,734; and 9,027,254 and U.S. Patent Application Publication Nos. 2008/0243141 and 2014/0276795 all of which are incorporated by reference herein for all purposes. What is needed is a device that includes a cold bladed scalpel that is convertible into bipolar forceps so that both can be used without switching between the two different devices. It would be attractive to have an interface that permits a scalpel to be connected to and removed from forceps or a medical device so that the scalpel and forceps or medical device may be used without switching therebetween. It would be attractive to have an interface that allows virtually any scalpel to be added and removed from forceps or a medical device. What is needed is an interface that permits a scalpel to be connected to forceps and then extended along the forceps for use and retracted along the forceps so that the forceps can be used. It would be attractive to have forceps that can be added to a scalpel and then the forceps moved longitudinally relative to the scalpel. What is needed is an interface that connects a scalpel to electrosurgical forceps and the interface prevents some or all of the therapy currents from passing from the forceps to the scalpel.

SUMMARY

The present teachings meet one or more of the present needs by providing: an interface comprising: (a) a first portion including: (i) a body portion that is configured to receive a portion of a scalpel and (ii) a channel that is configured to connect the scalpel to a surgical device.

The present teachings provide an electrosurgical device comprising: an interface comprising: (a) a first portion including: (i) a body portion that is configured to receive a portion of a scalpel and (ii) a channel that is configured to connect the scalpel to a surgical device; and (b) a second portion that is connected to the surgical device, the second portion including: (i) an interference tab that extends through the channel of the first portion to connect the first portion to the second portion and (ii) a track that extends through the channel so that the first portion can extend along the second portion.

The present teachings provide: a medical device comprising: a medical device comprising: (a) an interface including: (i) a first portion including: (1) a body portion configured to connect to a handle of a scalpel; and (2) a connection adapter; (ii) a second portion; wherein the connection adapter includes an interface portion that is a channel and the second portion includes an interface portion that is a tab that extends into the channel so that the first portion is connected to the second portion or wherein the second portion includes an interface portion that is a channel and the connection adapter includes an interface portion that is a tab that extends into the channel so that the first portion is connected to the second portion.

The present teachings provide: a medical device comprising: (a) an interface including: (i) a first portion including: (1) a body portion connected to a handle of a scalpel; and (2) a connection adapter; (ii) a second portion; wherein the connection adapter includes an interface portion that is a channel and the second portion includes an interface portion that is a tab that extends into the channel so that the first portion is connected to the second portion or wherein the second portion includes an interface portion that is a channel and the connection adapter includes an interface portion that is a tab that extends into the channel so that the first portion is connected to the second portion.

The present teachings provide: a medical device comprising: (1) a scalpel, and (2) an interface including a first portion that is integrally connected to the scalpel, wherein the first portion includes a connection adapter with an interface portion, the interface portion being a channel that is configured to receive a tab of a second portion to form a connection with the second portion.

The present teachings provide: a medical device comprising: (a) a second portion comprising: (i) a body, (ii) a first working arm, (iii) a second working arm connected to the first working arm by the body, and (iv) an interface portion extending from the body; wherein the interface portion extends cantilever from the body portion and is configured to extend into an interface portion of a first portion so that the first portion and the second portion are connected together.

The present teachings provide: an interface comprising: (a) a first portion comprising: (i) a body; (ii) a plurality of buttons located on the body; (iii) a power cord; (iv) a tab that is configured to receive and connect to the first portion to a second portion; and (v) a body portion configured to connect to a scalpel.

The present teachings provide: an interface comprising: (a) a first portion comprising: (i) a body, (ii) a plurality of buttons located on the body, (iii) a tab that is configured to receive and connect to the first portion to a second portion, and (iv) a body portion configured to connect to a scalpel, the body portion including: (1) a flap that is movable between an open position and a closed position so that a scalpel is connectable to and removable from the first portion, and (2) a locking device.

The present teachings provide: an interface comprising: (a) a first portion comprising: (i) a body, (ii) a tab that is configured to receive and connect to the first portion to a second portion, and (iii) a body portion configured to connect to a scalpel, the body portion including a power cord.

The present teachings provide: an interface comprising: (a) a first portion including: (i) a body, (ii) a first working arm connected to an extending from the body, and (iii) a second working arm connecting to and extending from the body from a side of the body opposite the first working arm, wherein the body includes a connection adapter with an interface portion that is a channel for receiving a portion of a second portion, and wherein the first working arm and the second working arm are movable about the body and the connection adapter to create a gripping force.

The present teachings provide: an interface comprising: (a) a first portion comprising: (i) a tab that is configured to receive and connect to the first portion to a second portion, and (ii) a body portion configured to connect to a scalpel, the body portion including: (1) a flap that is movable between an open position and a closed position so that a scalpel is connectable to and removable from the first portion, and (2) a locking device.

The present teachings provide a cold bladed scalpel that is convertible into bipolar forceps so that both can be used without switching between the two different devices. The present teachings provide an interface that permits a scalpel to be connected to and removed from forceps or a medical device so that the scalpel and forceps or medical device may be used without switching therebetween. The present teachings provide an interface that allows virtually any scalpel to be added and removed from forceps or a medical device. The present teachings provide an interface that permits a scalpel to be connected to forceps and then extended along the forceps for use and retracted along the forceps so that the forceps can be used. The present teachings provide forceps that can be added to a scalpel and then the forceps moved longitudinally relative to the scalpel. The present teachings provide an interface that connects a scalpel to electrosurgical forceps and the interface prevents some or all of the therapy currents from passing from the forceps to the scalpel.

DETAILED DESCRIPTION

Figure 1A:
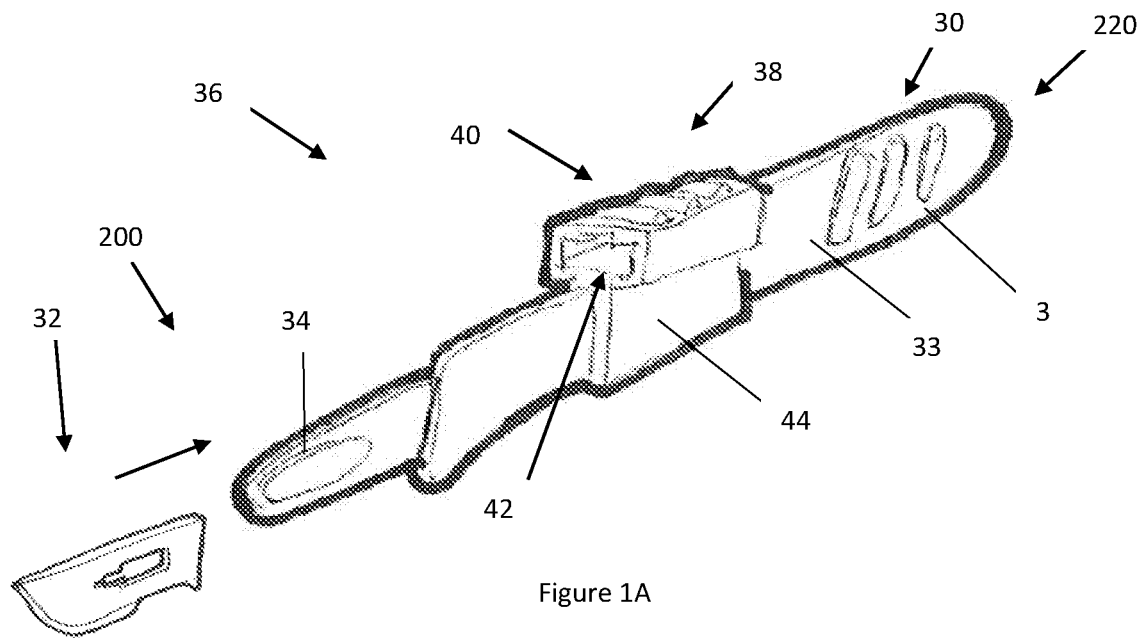
FIG. 1A illustrates a perspective view of a first portion of an interface and scalpel that are integral.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to an interface that functions to connect a scalpel to a medical device and/or connect a surgical instrument to a scalpel. The interface as taught herein may function to convert a scalpel into a medical device with increased functionality such as forceps, electrosurgical capabilities, or both. Preferably, the interface connects a cold blade scalpel to forceps or connects forceps arms to a cold blade scalpel. A single interface may function to connect a scalpel to a surgical device or vice versa. The interface may connect to any scalpel (e.g., any scalpel that can be used for surgery such as a single piece scalpel, a disposable scalpel, or a scalpel with a disposable blade). The scalpels may be a standard cold blade scalpel used for surgery. The scalpels may include an integral blade or the blade may be removable. The scalpel may include a handle that is incorporated into a portion of an interface (i.e., a first portion) or the handle may be integrally formed with a portion of the interface. The interface may allow for movement (e.g., longitudinal movement) of the scalpel and/or forceps between two or more positions (e.g., a proximal position and a distal position). The interface may allow for longitudinal movement of the scalpel relative to the medical device, one or more forceps arms, forceps, a second portion, a first portion, or a combination thereof. The interface may allow for longitudinal movement of the forceps relative to the medical device, the scalpel, the first portion, a second portion, or a combination thereof. The interface may prevent lateral movement (i.e., side to side movement) or rotational movement (i.e., movement about an axis). The interface may function to connect the scalpel to a working arm, between working arms, to a body portion, or a combination thereof. The interface may function to connect working arms on one or both sides of the scalpel. The interface may removably connect the scalpel or forceps to a surgical instrument forming a combination medical device as is taught herein. The interface may connect two surgical devices or surgical instruments (both of which are used interchangeably herein) together to form one medical device. The interface may include one or more ports that receive all or a portion of one or more surgical devices.

The one or more ports may be a mechanical connection, an electrical connection, or both. The one or more ports may include a female connector, a male connector, or a combination of both. The one or more ports may be and/or may include a plug receptor, a plug connector, or both. The port may be a portion of the interface that forms a connection so that one or more surgical devices may be added, removed, powered, mechanically controlled, electrically controlled, provide power, or a combination thereof. The one or more ports may act as a connection adapter, the teachings of the connection adapter are incorporated herein for the port. The interface may electrically insulate the scalpel from the surgical device and vice versa. The interface may be solid. The interface may be flexible or include one or more flexible pieces. The interface may be made of any biocompatible material. The interface may be made of plastic. The interface may be a single piece. Preferably, the interface is two pieces or two portions. More preferably, the interface does not include more than two pieces or two portions. The interface may be a plurality of pieces or portions. The interface may have one piece that has a flexible portion and one piece that is substantially rigid. The interface may have one piece that directly connects to a scalpel or is an integral part of a scalpel. The interface may have one piece that directly connects to a surgical instrument or is part of the surgical instrument. The interface may be an integral part of the forceps, the scalpel, the medical device, a surgical instrument, or a combination thereof. The interface may be removably attached to the forceps, scalpel, the medical device, a surgical instrument, or a combination thereof. The interface may connect one portion to a second portion so that a scalpel is connected to within a medical device. The interface may include a first portion (e.g., a scalpel portion), a second portion (e.g., a surgical device portion), or both for forming a medical device discussed herein. The first portion and the second portion may connect together to form a medical device and may be used individually as surgical instruments. For example, the first portion may connect to a scalpel and the second portion may connect to a forceps and individually the parts may be used, and when connected the parts may be used at times and disabled at times depending upon a selection by a user.

The first portion may function to connect a surgical instrument to another portion of an interface, another surgical instrument to form a medical device, a scalpel to a medical device, or a combination thereof. The first portion may connect to forceps, one or more working arms, a rotatable cutting tip, a suction source, or a combination thereof. Preferably, the first portion may function to connect to a scalpel. The first portion may function to connect to a second portion, a surgical device, or both. The first portion may attach to a scalpel and then attach to a second portion or a surgical device. The first portion may extend fully or partially around one or more portions of a scalpel. The first portion may connect to a handle of a scalpel. The first portion may be an integral part of a scalpel or a scalpel handle. The first portion may receive a portion of the scalpel and once received the scalpel may be prevented from moving relative to the first portion. The first portion may form a fixed connection with the scalpel and a movable connection (directly or indirectly) with the medical device or second portion so that the scalpel is movable relative to the medical device or the second portion. The first portion may be movable between a distal position and a proximal position relative to the second portion or the medical device or vice versa. The first portion may move between a distal position and a proximal position and when in one or both of the positions may cover or uncover one or more buttons. For example, when the first portion is in the distal position the first portion may cover a first button and a second button may be exposed, and when moved to a proximal position the first button may be exposed and the second button may be covered. The first portion may be powered. The first portion may be free of power. The first portion may be battery powered. The first portion may be connected to a power cord that supplies power to the first portion, the second portion, the medical device, or a combination thereof. The first portion may include one or more buttons or a plurality of buttons. The first portion may be free of buttons. The first portion may be an integral part of a scalpel. The first portion may have one or more connection adapters, one or more interface portions, one or more body portions, one or more flaps, one or more enclosures, or a combination thereof.

The one or more flaps may function to create a space that receives all or a portion of a surgical instrument so that the first portion and the surgical instrument are connected together. The one or more flaps may function to receive a handle of a scalpel so that the scalpel and the first portion are connected together. The one or more flaps may be movable relative to the first portion so that a surgical instrument (e.g., a scalpel) can be inserted into the first portion and connected to the first portion. The one or more flaps may be movable between an open position and a closed position. The one or more flaps may rotate about a hinge, slide along a track, slide laterally, slide longitudinally, slide within a slit, be completely removable, or a combination thereof. The one or more flaps may be movable to expose an enclosure that receives a portion of a surgical instrument and then closes again once the flap is moved into place so that the surgical instrument has a portion that is substantially enclosed or a portion that is entirely enclosed within the enclosure.

The enclosure may be a portion that receives part of a surgical device so that the surgical device can be added and removed from the first portion. Preferably, the enclosure is shaped and sized to fit a particular surgical device (e.g., a handle of a scalpel). The enclosure may be opened and closed to receive a portion of a surgical instrument. The enclosure may be a formed enclosed space and once a surgical instrument is placed in the enclosure, the enclosure may move to hold the surgical instrument within the enclosure. For example, the enclosure may be rigid and include a malleable material that forms a friction fit with a portion of the surgical instrument so that the surgical instrument is locked within the enclosure. The enclosure may allow for some movement of the surgical device relative to the first portion. Preferably, the enclosure maintains the surgical device substantially static (e.g., may allow some movement of the surgical instrument due to flexing of the materials of the enclosure) or completely static relative to the first portion. The enclosure may be located proximate to one or more connection adapters.

The one or more connection adapters may function to receive a portion of a second portion, a first portion, a surgical device, or a combination thereof. The one or more connection adapters may connect a first portion to a second portion so that a medical device is formed. The one or more connection adapters may function to extend into a portion of a second portion, a surgical device, a first portion, or a combination thereof. The one or more connection adapters may function to receive a portion of a second portion, a surgical device, a first portion, or a combination thereof. For example, a first portion may have a connection adapter that extends into a connection adapter of a second portion. The one or more connection adapters may connect the first portion to the second portion. The one or more connection adapters may fixedly connect or movably connect a surgical instrument (e.g., a surgical device) and a scalpel. The connection adapter may be one solid piece. The connection adapter may be multiple pieces. The connection adapter may be a flexible or movable piece. The connection adapter may include a lock, a piece that is movable to fix the scalpel, forceps, surgical device, or a combination thereof in a position. The connection adapter may include one or more gripping features to assist in moving the first portion relative to the medical device or the second portion. The one or more connection adapters may be a port, through hole, male piece, female piece, tab, or a combination thereof. For example, the connection adapter may be a port when the connection adapter provides power to a surgical device. The port may mechanically connect, electrically connect, or both a first portion and a second portion. The port may be a female portion, a male portion, or both. The port may me part of the first portion, the second portion, or both the first portion and the second portion may include a port. The port may include or be a plug receptor, a plug connector, or both.

The plug receptor may receive all or a portion of a surgical device to create a mechanical connection, an electrical connection, or both. The plug receptor may be a recess that a plug connector extends into. The plug receptor may be a female part. The plug receptor may surround all or a portion of a surgical device, a plug connector, or both. The plug receptor may be a connection adapter. Preferably, the plug receptor powers one or more of the surgical instruments and assists in providing a mechanical connection within the medical device. The plug receptor may include both electrical features and mechanical features. For example, the plug receptor may be a twist to lock system and once locked in place the electrical features may be enabled. The plug connector may snap into the plug receptor.

The plug connector may function to fit within the plug receptor to form an electrical connection, a mechanical connection, or both. The plug connector may assist in connecting two parts together (e.g., a surgical device and a second portion). The plug connector may be a connection adapter that both forms a physical connection and provides power to a portion of the surgical instrument, first portion, second portion, or a combination thereof. The plug connector may have prongs that extend into the plug receptor. The plug connector may allow a surgical device such as forceps to snap into a second portion and be used as forceps. The plug connector may be a male part. The plug connector may be a connection adapter that is part of the surgical device, the second portion, or both. The connection adapter may include one or more interface portions. The plug connector, the plug receptor, or both may directly or indirectly connect to a power cord.

The power cord functions to supply therapy signals, therapy currents, voltage, current, power, signals, or a combination thereof to a first portion, a second portion, a scalpel, forceps, or a combination thereof. The power cord may be connected into a first portion or a second portion. The first portion, the second portion, or both may be free of a power cord. The power cord may be located internally and may connect a battery supply to a location of interest.

The one or more interface portions may function to connect the first portion to a surgical device, a second portion, or both. The one or more interface portions may function to connect forceps or a surgical device to a scalpel, a first portion, a second portion, or a combination thereof. The one or more interface portions may function to create a movable connection between the scalpel and the surgical device, the forceps, or both. The one or more interface portions may receive a portion of the surgical device, the second portion, or both. The one or more interface portions may extend into a portion of the surgical device, the second portion, or both. Both the first portion and the second portion may include an interface portion. Preferably, both the second portion and the first portion include interface portions and the interface portions form a mating relationship so that the scalpel and the forceps or the medical device are connected together. The one or more interface portions may allow a body portion to move relative to the interface portion. For example, the interface portion may connect to the surgical device and form a fixed connection with the surgical device so that the interface portion does not move relative to the surgical device and the body may move relative to the interface portion. When each of the first portion and the second portion include an interface portion, the interface portions are complementary to each other. For example, one interface portion is a male part and the other interface portion is a female part. The interface portions may be a channel, a tab, or both. The interface portions may include a channel that is a through hole. The interface portion may include a tab. The channel may receive all or a portion of a tab of another part of the interface, surgical device, forceps, scalpel, or a combination thereof. The channel may include one or more grooves.

The one or more grooves may be complementary to a track. The track may function to allow movement relative to the first portion and the second portion. The track may form a support for one or more rails. The track may permit longitudinal movement and prevent lateral movement, rotational movement, or both. The track may be a planar surface that permits one portion to move relative to the other portion. The one or more rails or grooves (grooves and rails as discussed herein are used interchangeably) may receive all or a portion of the track. The one or more grooves may be generally "C" shaped, generally "I" shaped, or generally "H" shaped, to hold a portion of a track. The one or more grooves may have a top and a bottom and the top and bottom may contact the track forming a friction fit. The one or more grooves may function to ride on the track so that the first portion moves relative to the second portion. The one or more grooves may be located at a bottom of the interface portion so that the interface portion is projected above the grooves. The one or more grooves may be located at a top of the interface portion so that the interface portion hangs from the grooves. The channel may have a bearing surface so that the channel can be used to move the scalpel relative to the forceps, medical device, or both or vice versa. The channel may have a uniform dimension (i.e., length, width, height). The dimensions of the channel may vary along the length, width, height, or a combination thereof. The channel may include one or more movable parts that may temporarily lock one device relative to another device (e.g., forceps or a scalpel). The channel may include one or more locking devices so that the first portion and the second portion may be locked relative to each other. The interface portion may be connected to one or more body portions.

The one or more body portions may function to connect the first portion to one or more scalpels. The one or more body portions may surround a portion of a scalpel so that the first portion and the scalpel are connected together. The body portion may receive a portion of a scalpel (e.g., handle) so that the scalpel is connected to the body portion. The handle and the body portion may be one integral piece. The body portion may receive a portion of the scalpel so that the scalpel may be removed from the body portion. The one or more body portions may be a plurality of bodies. The one or more body portions may be a single body. The body portions may include a through hole. The body portions may be an outer shell that extends around and surrounds a length of the scalpel. Preferably, the body portion is connected to the handle of a scalpel. The body portion may be a central part of a first portion, a second portion, or both. The body portion may be a part that all of the other pieces of the first portion, the second portion, or both are connected to and extend from. The outer shell may form a complete periphery (e.g., the outer periphery may extend 360 degrees around the scalpel). The outer shell may form an enclosure or be an enclosure as is discussed herein. The outer shell may be an integral part of the scalpel, the forceps, a surgical instrument, or a combination thereof. The outer shell may form a partial periphery (e.g., the outer periphery may extend less than 360 degrees around the scalpel) around an outer surface of the scalpel. The outer shell may extend about 90 degrees or more, about 120 degrees or more, about 180 degrees or more around an outer surface of a scalpel. The outer shell may extend about 360 degrees or less, about 300 degrees or less, or about 275 degrees or less around an outer surface of the scalpel. The outer shell may be square, rectangular, U-shaped, V-shaped, have an open bottom, have an open top, be a box structure, be octagonal, pentagonal, heptagonal, hexagonal, or a combination thereof. The outer shell may be tapered (e.g., a front side of the opening may be larger than a rear side opening or vice versa). The outer shell of the body portion may include one or more seals or gripping devices on the inside that assist in gripping a scalpel. The through hole in the outer shell of the body may include the seals or gripping devices. The body portions may be movable to grip and release a scalpel, forceps, a surgical instrument, or a combination thereof. The body portions may include a lock that locks a scalpel in place (e.g., a flap). The outer shell of the body portions may form a friction fit with a scalpel. The outer shell of the body portions may include a high friction portion (e.g., rubber) to maintain the scalpel within the body portions. The outer shell of the body portions may have a length, width, and height. The length may be sufficiently long to grip a scalpel and inhibit or prevent movement of the scalpel relative to the body. The width and height may be substantially the same as the scalpel so that a friction fit is formed between the body and the scalpel. The body portion may include one or more locking devices.

The one or more locking devices may function to connect one or more forceps arms, a forceps, a medical device, scalpel, surgical instruments or a combination thereof to a first portion, a second portion, or both. Preferably, the locking arms receive and connect a working arm to a side of a scalpel so that the scalpel is located between working arms. The locking devices may be located on a first side, a second side, or both of the body portion, a flap, a first portion, a second portion, or a combination thereof. A first working arm may connect to the locking device on the first side and a second working arm may connect to the locking device on the second side. The one or more working arms may be added and removed from a scalpel, a first portion, or both by the locking devices. The one or more locking device may be spring loaded. The one or more locking devices may be rigid. The one or more locking devices may allow for the working arms to pivot about the first portion. The one or more locking devices may lock the working arms into contact with the blade of the scalpel when the scalpel is extended. The one or more locking devices may immobilize the working arms, the scalpel, or both. The one or more locking devices may be a clip, a one way feature, a snap feature, a bias feature, a springing device, or a combination thereof. The one or more locking devices may place a bias force on the working arms. The one or more locking devices may individually place a bias force on each of the working arms, or the locking devices may work together to create an equal bias on each of the working arms. The one or more locking devices may function as a second locking feature (e.g., the interface portion may include the first locking feature). The one or more locking devices may assist in connecting the first portion to the second portion.

The second portion may function to connect to a surgical device, connect a first portion to a surgical device, or both. The second portion may function to connect a scalpel into a surgical device, forceps, or both. The second portion may be an integral part of a surgical device. The second portion may be added to a surgical device. The second portion may permit the scalpel to be added and removed from the surgical device. The second portion may include one or more interface portions as is discussed herein. The interface portion of the second portion may be a tab, a channel, or both.

The tab may function to connect two parts of the interface together. The tab may function to extend into a channel. The tab may function to lock into a channel. For example, once the tab is extended into a channel, the tab may prevent removable of the part the tab is connected to from being removed from the channel. The tab may be a complementary part to an interface portion of another part of the interface. The tab may be a male member. The tab may extend into a channel. The tab may be unidirectional (i.e., may be inserted in one direction and prevent removal in a second opposing direction) so that the first portion is connected to the second portion in a first direction and prevented from being removed in a second opposing direction. The tab may be movable. The tab may be solid. The tab may be located at a proximal end, a distal end, or both ends of a connection adapter, an interface portion, or both. For example, a first portion or a second portion may include two tabs that oppose each other so that the first portion or the second portion may move between the opposing tabs but may be prevented from being moved past the tabs. The tab may be generally "C" shaped. The tab may have a one or more curved portions and planar portion. The tab may have two curved portions that are connected by a linear portion or a main part. The tab may include a part that is folded back upon itself. The tab may be curved. The main part may be flat, linear, planar, extend in a single plane, be connected to one or more locking parts, two locking parts, or a combination thereof. The tab may have a main part and a locking part that extends back towards the main part and the locking part extends at an angle relative to the main part. For example, the locking part may curve about 320 degrees more so that the locking part and the main part form an angle. The locking part and the main part may be one integral piece. The locking part and the main part may be separated by an angle of about 5 degrees or more, about 10 degrees or more, about 15 degrees or more, or even about 25 degrees or more. The locking part and the main part may be separated by an angle of about 90 degrees or less, about 75 degrees or less, or about 60 degrees or less. The locking part may flex relative to the main part.

The locking part may extend from a main part. The locking part may extend at an angle relative to a main part. The locking part may have one direction that passes through an opening and a second direction that catches the opening and locks the tab to the opening. For example, the locking part may be "C" shaped or "V" shaped and the locking part may flex to form a connection and the elastically deform so that locking part conforms to its shape so that the tab is locked to a channel, a connection adapter, or both. The locking part may flex a sufficient amount (i.e. about 1 degree, about 2 degrees, or even about 5 degrees) relative to the main part so that the tab may fit through a channel to connect the first portion to the second portion. The tab may be spring loaded. The tab may be made of a plastically deformable material. The tab may include elastically deformable portions. The tab may be made of plastic, metal or both. The tab may be a barbed tab that extends through a channel and expands to form a connection. The main part of the tab may include a track or be a track.

The track may function to allow one part to move relative to another part. The tab may function to support another part of the medical device. For example, if the first portion includes a track and the second portion includes a rail then the second portion may be connected to the first portion by the rail and track. Preferably, the track functions to allow a second portion to move relative to a first portion or vice versa. The track may support a rail by suspension (i.e., may hang below the track) or the rails may ride upon the track (i.e., the rails are located above the track). The track may function to fit within a groove. The track may function to fit within a channel and permit movement of the first portion and the second portion relative to each other. The track may be generally "T" shaped. Each side of the track may fit within a groove. The track may have a bearing surface to allow for the grooves to slide along the track. The track may have a friction surface that prevents easy movement along the track. The track may support the interface portion so that the interface portion extends over one or more of the buttons of the medical device. The track may be located proximate to the one or more buttons. The track may extend along all or a portion of the medical device, the connection adapter, the interface portion, or a combination thereof. Preferably, the track is substantially the same length as the length of the medical device that includes buttons. The track may extend along about 75 percent or less, about 60 percent or less, about 50 percent or less, or about 30 percent or less of the medical device. The track may extend along about 10 percent or more, about 15 percent or more, or about 25 percent or more of the medical device.

The interface as discussed herein may be used to incorporate a scalpel, forceps, a surgical device, or a combination thereof into a medical device or to form a medical device. Medical device as discussed herein is a product of using the interface to connect one or more surgical instruments together. The medical device as discussed herein may be a combination surgical instrument (i.e., a device that includes a plurality of surgical instruments that may be used individually but are combined together into a single device). The interface may add components to a scalpel to form a medical device. The interface may add components to forceps to form a medical device. The medical device may function to grip, cut, cauterize, electrically cut, seal, coagulate, or a combination thereof. The medical device may be used during open surgery to assist a surgeon in performing a surgical procedure. The medical device may include a distal end (i.e., a part farthest from the surgeon) and a proximal end (i.e., the part closest to the surgeon or gripped by a surgeon). The medical device may include one or more components that are movable between a distal position and a proximal position. The medical device may include forceps, a scalpel, or both. The components in the distal position are located farther from the surgeon then when the components are in the proximal position. The forceps, blade, first portion, second portion, or a combination thereof may be movable between a distal position and a proximal position. The medical device may be an electrosurgical device. Preferably, the medical device is an electrosurgical device that is configured to pass power through a portion of the medical device, the scalpel, the forceps, one or both working arms, or a combination thereof.

The present teachings relate to an electrosurgical device that may be part of an electrosurgical system. Preferably, the present teachings relate to an electrosurgical device and associated componentry that form an electrosurgical system. The electrosurgical system may be any system that includes one or more of the devices taught herein. Preferably, the electrical surgical system includes at least an electrosurgical device. The electrosurgical system may include one or more medical devices as taught herein, one or more ground pads, one or more generators, one or more electrosurgical devices, or a combination thereof and the teachings herein of each device which are incorporated into the electrosurgical system. Preferably, the medical device as taught herein is connected to a generator, a ground pad, or both. The electrosurgical device may be any device that may be used by a surgeon to perform a surgical procedure. The electrosurgical device may function to be switched between two or more configurations, two or more states, or both. The electrosurgical device may be switched between a monopolar configuration, a bipolar configuration, a non-electrosurgical configuration, or a combination of the three. The electrosurgical device may be used ambidextrously, ambidextrously switched between configurations, or both. The electrosurgical device may be used to cut, perform hemostasis, coagulate, desiccate, fulgrate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, the like, or a combination thereof. In another example, one or more parts of the device may include a sharp edge and may be used to cut, similar to that of a scalpel. The electrosurgical device may include a generator or be connected to a generator. The electrosurgical device may have one or more therapy signals that extend between the medical device and the generator.

The one or more therapy signals may be a signal, power, continuity, or a combination thereof. The one or more therapy signals may extend from the medical device to the generator or vice versa. The one or more therapy signals may be formed by the medical device, formed by the generator, or both. The electrosurgical therapy signals may be a therapy current. Preferably, the electrosurgical therapy signals indicate that a user has performed a step and a signal is being transmitted so that therapy current, energy, or both is generated. The electrosurgical therapy signals may provide a signal so that one or more therapy currents are produced and the therapy currents may be used for electrosurgery. The electrosurgical therapy signal may be a monopolar therapy signal, a bipolar therapy signal, or both. The monopolar therapy signal may be any signal that has a voltage differential between a return port and an active port in the generator. The monopolar therapy signal may be any signal that when applied by the electrosurgical device extends from one pole of an electrosurgical device to another pole located at a remote location, from the electrosurgical device, from the medical device, or a combination thereof. For example, a monopolar therapy current may extend from a scalpel to a ground pad. The bipolar therapy signal may be any signal that has a voltage differential between two leads that are connected to the electrosurgical device, that are located in the generator, or both. The bipolar therapy signal may be any signal that when applied by the electrosurgical device extends from one component of a medical device to another component of the medical device (e.g., between two working arms, from a scalpel to one or both working arms, or both). An electrosurgical therapy signal, when the activation circuit is in the second state, may exit the medical device so that a therapy current extends from a scalpel, between the first working arm and the second working arm, between the scalpel and one or both of the working arms, or a combination thereof. The therapy signal may be generated and conducted from the medical device to the generator.

The non-electrosurgical configuration may be any configuration where power is not supplied to the medical device, the scalpel, the two or more working arms, a surgical instrument, or a combination thereof. The non-electrosurgical configuration may be used when the electrosurgical device is being used as forceps, tweezers, a scalpel, a clamp, Kelley hemostat forceps, or a combination thereof. In the non-electrosurgical configuration the working arms may be mobile. In the non-electrosurgical configuration the working arms may be immobilized, may immobilize the scalpel, a cutting arm, an extendable arm, or a combination thereof. The cutting arm, the extendable arm, or both may be the scalpel, may be a discrete arm that includes a sharp edge and may be alternated with the monopolar arm, or both. The non-electrosurgical configuration may be switched to a monopolar configuration or a bipolar configuration by pressing a button, turning a switch, advancing a cutting arm, advancing a scalpel, advancing an extendable arm, or a combination thereof.

The device when in a monopolar configuration may supply power through a medical device component (e.g., a scalpel) and a return electrode that may be located at another location outside of the hand held portion of the electrosurgical device, through a medical device component and an adjacent medical device component, or both. The monopolar configuration may be any configuration where the electrosurgical device may be used to apply monopolar power. The monopolar configuration may be used to cut tissue, coagulate blood and/or fluids, electrical cutting, hemostasis, apply power to a large area, or a combination thereof. The monopolar configuration may be used to heat a specific area, heat an object between both electrodes, in contact with both electrodes, or a combination thereof. A monopolar configuration may be used so that power during use extends from a scalpel to one or both bipolar electrodes (i.e., both working arms), one or more ground pads, or a combination thereof so that the scalpel may be used for delicate electrosurgery, localized electrosurgery, coagulation, cutting, or a combination thereof. The scalpel may be electrically powered (i.e., monopolar electrosurgery) for less delicate procedures, less localized electrosurgery, or both when compared to bipolar electrosurgery.

The device when in a bipolar configuration (i.e., when configured as forceps) may supply power from one portion of the device to a second portion of the device so that the return path for the power is relatively short when compared to the monopolar configuration. The bipolar configuration may be any configuration where the electrosurgical device may be used to apply bipolar power. The device when in the bipolar configuration may supply power between two localized medical device components such as two working arms. The bipolar configuration may be used to coagulate, for hemostasis, cutting, fulguration, or a combination thereof. When in the bipolar configuration the electrosurgical device may include two opposing working arms. The two opposing working arms may be configured as forceps.

The scalpel may be used to apply monopolar power during a procedure, and the scalpel may be longitudinally movable, rotationally movable, extendable, retractable, or a combination thereof. The scalpel may be free of any direct power. The scalpel may be free of leads, wires, cords, or a combination thereof that directly power the scalpel. The scalpel may be powered through one or both of the working arms contacting a portion of the scalpel and power passing through the scalpel. The scalpel may be located between a first working arm and a second working arm. The scalpel may be static. The scalpel may be static and one or both of the working arms, the forceps, or both may be movable longitudinally relative to the static (e.g., this may be in addition to the lateral movement of the forceps to create a gripping force). The scalpel may have a first position (e.g., retracted) and a second position (e.g., extended). The first position may be where the scalpel is located relative to the working arms so that the working arms are past the scalpel (e.g., the scalpel is retracted so that the working arms extend past the scalpel or the working arms are extended so that the working arms extend past the scalpel). The first position may be where the scalpel is electrically disconnected, electrically shorted relative to another medical device component, electrically insulated so that power cannot pass from the scalpel, or a combination thereof. In the first position, the scalpel may be located so that the working arms can move towards each other and into contact without a gripping area of the working arms being impeded by the scalpel. The second position may be where the scalpel is located relative to the working arms so that the scalpel is extended beyond the working arms (e.g., the scalpel is extended so that the working arms are located proximate to the user or the working arms are retracted so that the scalpel is beyond the working arms). The second position may be where the scalpel is electrically connected, supplies a therapy current, is electrically continuous, or a combination thereof. The scalpel may be a separate piece that when activated may be used to supply monopolar power. The scalpel may be used for electrically cutting, mechanically cutting, or both.

The electrosurgical device may include one or more buttons. Preferably, the electrosurgical device includes a plurality of buttons. The buttons may include a forward activation button, a first activation button, a second activation button, or a combination thereof. The buttons may turn on a monopolar therapy current, a bipolar therapy current, or both. The activation buttons may each activate other functions such as ultrasound, heating, cooling, rotation, gripping, opening of working arms, closing of working arms, reciprocation of a scalpel, movement of a scalpel distal and proximal, movement of working arms distal and proximal, power, waveforms, or a combination thereof. Each of the activation buttons may be switched between one or more of the functions discussed herein depending on the configuration of the working arms, the blade, or both. The medical device may be forceps that include a scalpel.

The forceps may function to grip, hold, squeeze, or a combination thereof one or more objects. The forceps may include one or more finger grips (i.e., configured like scissors) that may be used to move the forceps so that they may be used to grip one or more objects. The forceps, first portion, second portion, or a combination thereof may include a forceps portion. The forceps portion may be a part of a forceps but the forceps portion may require a portion of the first portion or the second portion to operate. For example, the body portion of the forceps may be the first portion that connects the two working arms together. The forceps, forceps portion, or both may include one or more working arms. The one or more working arms may create a gripping force, provide a therapy current, disable a scalpel, or a combination thereof. The one or more working arms may be half a forceps and may move to create a gripping force. Preferably, the working arms are a first working arm and a second working arm. The one or more forceps may be longitudinally static (i.e., do not slide along a longitudinal axis of the medical device). The one or more forceps may be longitudinally movable along the longitudinal axis of the medical device, the scalpel, or both. The one or more forceps may be laterally movable (i.e., the working arms may move in a straight line towards and away from each other to create a gripping force). The working arms of the forceps may be free of rotational movement. The forceps may be free of finger grips and be actuated by direct pressure being applied to opposing sides of the forceps so that the forceps close and grip an object. The forceps include at least two working arms. The forceps may include a body that connects the two working arms together. The body may be a hand piece, the first portion, the second portion, a connection adapter, an interface portion, or a combination thereof. However, the forceps may be free of a body and the working arms may be connected to a body portion of the first portion to form forceps.

The working arms may function to grip, hold, squeeze, or a combination thereof an object when the object is between the two or more opposing working arms. The working arms may include one or more gripping features that may assist in gripping, holding, squeezing, or a combination thereof an object. The working arms may be movable between two or more positions. Preferably, the working arms are movable between at least a first position and a second position. For example, the working arms may be movable between a bipolar configuration (e.g., first position) and a monopolar configuration (e.g., second position). The working arms may be movable longitudinally along the medical device (i.e., between the distal end and the proximal end). Preferably, the forceps are movable from a distal position where the forceps extend beyond the blade of the scalpel to a proximal position where the blade extends beyond the ends of the working arms. However, the working arms may be static and the blade may move relative to the working arms. The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other working arm, or a combination thereof. More preferably, in the second position the working arms are immobilized so that the working arms cannot be used a forceps. The working arms may be longitudinally static and moveable relative to each other. The working arms may be longitudinally moveable and may be moveable relative to each other so that a gripping force may be created. For example, the working arms when in a bipolar configuration may both be extended and then retracted so that a scalpel may be exposed forming a monopolar configuration. The working arms may be retractable and/or extendable individually, simultaneously, or both. The working arms may be selectively retractable and/or extendable so that one or more tip regions are exposed.

The working arms may include a tip region. The tip region may include a portion that is configured to assist in facilitating gripping, holding, squeezing, or a combination thereof. Additionally, the tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. The tip region may include a planar surface. The tip region (or gripping portion (i.e., the portion that contacts the blade or tissue when the working arms are moved towards each other)) may be free of a channel (e.g., a knife channel or a blade channel). The tip region of the first working arm and the second working arm may contact a portion of the scalpel and lock the scalpel in place when the scalpel is moved into a distal position. Preferably, the tip region includes insulation on the non-contact portions of the working arms so that electrosurgical energy is not transferred through incidental contact. The working arms may include an active portion and an inactive portion (i.e., an insulated portion). The working arms may extend on either side of a scalpel.

The scalpel may be a cold blade scalpel. The scalpel may function to cut. The scalpel may function to provide electricity. The scalpel may be free of electrical connections, leads, or a combination thereof. The scalpel may be free of wires that extend through the scalpel. The scalpel may be free of any electrical portions or devices to provide power (e.g., a monopolar therapy current, a bipolar therapy current, or both). The scalpel may include a portion or be made of a material that conducts electricity. The scalpel may be directly powered (i.e., a power cord may extend into the scalpel). The scalpel may extend and retract (i.e., move between a distal position (e.g., away from the user) and a proximal position (e.g., towards a user)). The scalpel may include a blade and a handle.

The handle may function as a gripping portion. The handle may function to connect the scalpel to an interface, the first portion, the second portion, a medical device, or a combination thereof. The handle may extend into an enclosure. The handle may be integrally molded with the first portion or the second portion. The handle may function to hold one or more blades via a blade receptacle. The scalpel may include removable blades. The blade receptacle may function to hold and release blades so that blades can be interchanged. The scalpel may be free of blade receptacles.

The one or more blades may function to cut. The one or more blades may have a sharp edge. The one or more blades may have a sharp side and a dull side. The one or more blades may be added to and removable from the scalpel. Preferably, the blades are removable from the handle of the scalpel.

The surgical instruments may be a scalpel, forceps, rotating blade, probe, ultrasound probe, or a combination thereof.

FIG. 1A illustrates a surgical instrument 3 that is a cold blade scalpel 30 having a blade 32 at a distal end 200 and a handle 33 extending from the blade 32 to a proximal end 220. The scalpel 30 is integrally connected to a first portion 38 of an interface 36 (the second portion of the interface 36 being shown in FIG. 1B). The cold blade scalpel 30 has a distal end 200 with a blade receptacle 34 that accepts blades 32 so that the blades 32 can be changed (the blade may be a fixed blade (not shown)). As shown, a blade 32 is being added to the scalpel 30. The connection adapter 40 includes an interface portion 42 that as shown is a channel. The interface portion 42 is located above a body portion 44 that is connected to the handle 33 of the scalpel 30. As shown, the handle 33 extends into a body portion 44, and the handle 33 is fixedly attached (e.g., molded) within the body portion 44 so that the first portion 38 and the scalpel 30 are formed as a single piece so that the scalpel 30 is connected to the first portion 38.

Figure 1B:
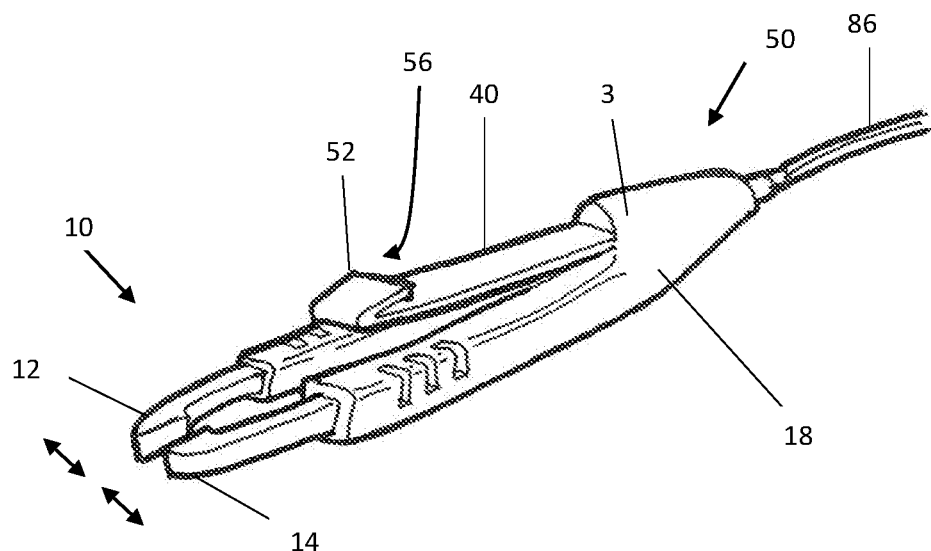
FIG. 1B illustrates a second portion of interface and forceps that are integral.
Figure 1C:
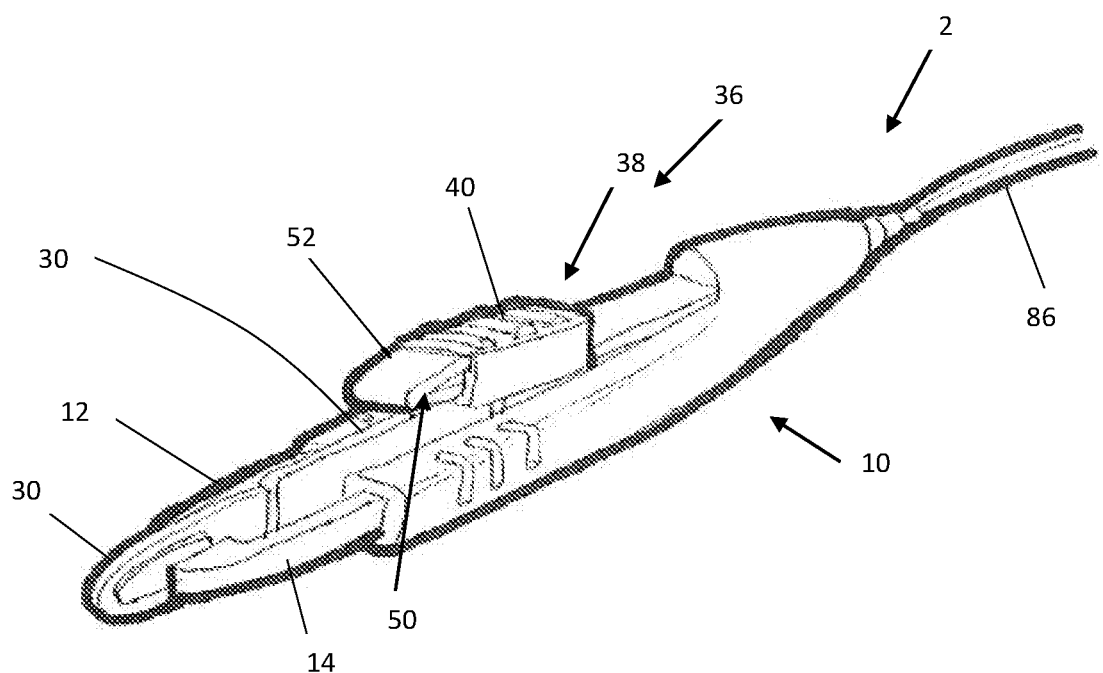
FIG. 1C illustrates the first portion of FIG. 1A connected to the second portion of FIG. 1B forming a medical device.

FIG. 1B illustrates a perspective view of a second portion 50. The second portion 50 includes a surgical instrument that is forceps 10 that are integral with a connection adapter 40. The forceps 10 have a first working arm 12 and a second working arm 14, which are connected together at a body 18 and the first arm 12 and the second arm 14 pivot about the body 18 so that the first arm 12 and the second arm 14 are movable towards and away from each other as indicated by the arrows to create a gripping force. The body 18 receives a power cord 86 so that power extends into the forceps 10 and through the first working arm 12, the second working arm 14, or both. A connection adapter 40 extends from the body 18. The connection adapter 40 includes a tab 52 that forms a locking part 56 so that a first portion (not shown) is movably locked to the second part 50.

FIG. 10 illustrates a medical device 2 where the first portion 38 of FIG. 1A and the second portion 50 of FIG. 1B are connected together forming an interface 36 so that the cold blade scalpel 30 is incorporated into forceps 10. As shown, the interface 36 includes a first portion 38 connected to the scalpel 30 and a second portion 50 connected to the forceps 10. The first portion 38 has an interface portion 40 that receives a tab 52 of a second portion 50 so that the scalpel 30 and the forceps 10 are moveably connected together so that the first portion 38 is movable longitudinally along the second portion 50 so that the scalpel 30 is moved distally of the first working arm 12 and second working arm 14 and proximally of the first working arm 12 and second working arm 14. The tab 52 extends through the interface portion 42 of the first portion 38 and then locks the scalpel 30 to the forceps 10 between the first working arm 12 and the second working arm 14. As shown, the medical device 2 is free of finger switches on the forceps 10, the scalpel 30, the first portion 38, and the second portion 50. The surgical device 2 is controlled by a foot petal (not shown) or switches on a generator (not shown). The first working arm 12, the second working arm 14, the scalpel 30, or a combination thereof are powered by the power cord 86.

Figure 2A:
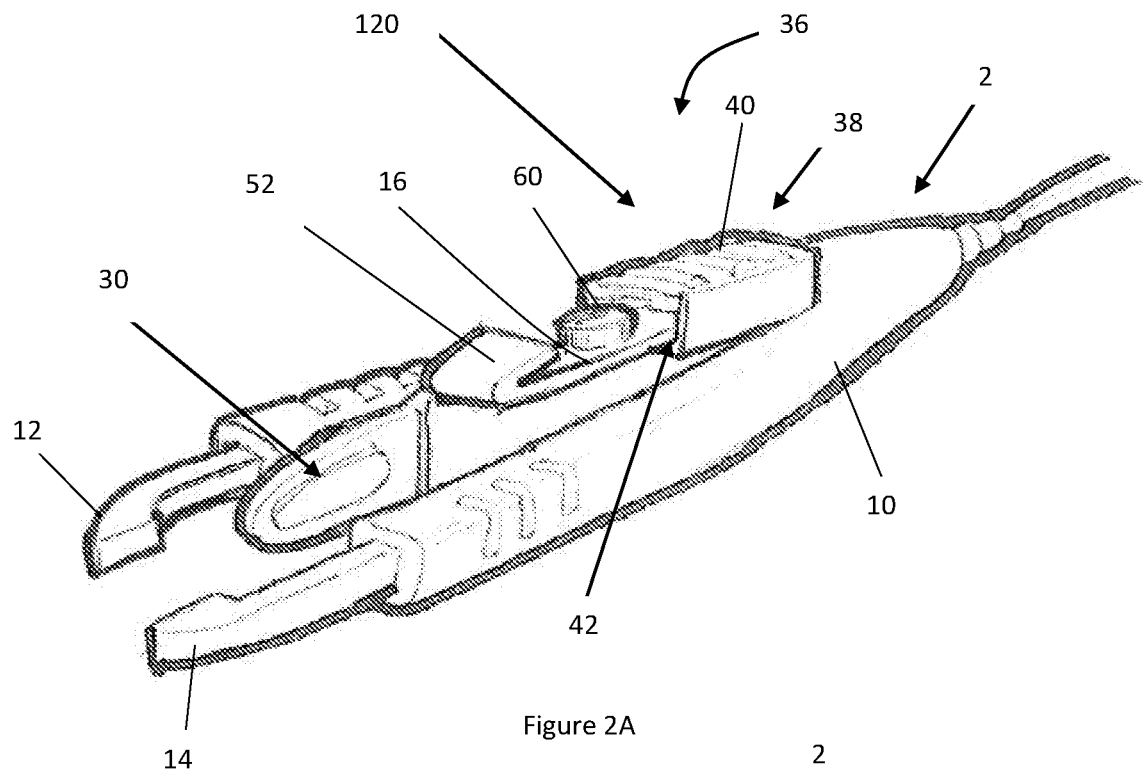
FIG. 2A illustrates the scalpel retracted (proximal position) so that a button is exposed in front of the interface.

FIG. 2A illustrates the medical device 2 with the cold blade scalpel 30 connected to the forceps 10. The scalpel 30 is incorporated into the forceps 10 by an interface 36. The interface 36 includes a first portion 38 and a second portion 50. The first portion 38 has an interface portion 42 that is a channel, which receives a tab 52 of the second portion 50 and that is movable along a track 16 of the tab 52. The connection adapter 40 is located in a proximal position 120 so that the scalpel 30 is located in a proximal position where the forceps arms are movable and a forward activation button 60 is exposed. As shown, when the connection adapter 40 is moved into the proximal position 120. In the proximal position 120, the forceps 10 and the scalpel 30 are moved relative to the forceps 10 so that the scalpel 30 extends to a location proximal of the ends of the forceps 10 so that the first working arm 12 and the second working arm 14 are movable relative to each other.

Figure 2B:
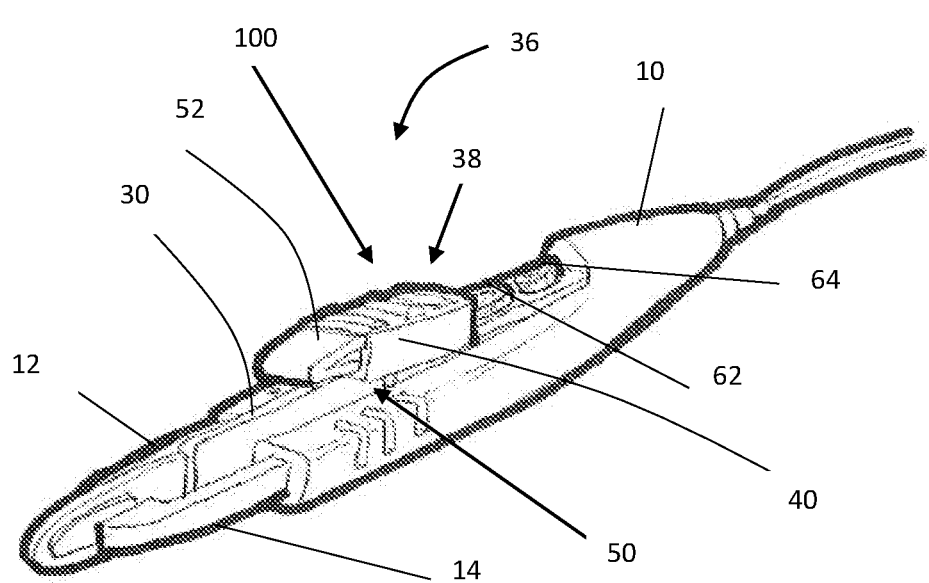
FIG. 2B illustrates the scalpel in extended (distal position) so that buttons are exposed behind the interface.

FIG. 2B illustrates the medical device 2 with the cold blade scalpel 30 connected to the forceps 10 by an interface 36 that includes a first portion 38 and a second portion 50. The first portion 38 is located in the distal position 100 and the first activation button 62 and the second activation button 64 are exposed, and the scalpel 30 is advanced so that the scalpel 30 extends distal of the first working arm 12 and the second working arm 14. The scalpel 30 is retained in the medical device 2 by the connection adapter 40 extending over the tab 52 and the tab 52 prevents the first portion 38 from being removed second portion 50. Further, the first working arm 12 and the second working arm 14 immobilize the scalpel 30. The first working arm 12 and the second working arm 14 may be deactivated in the distal position 100. A therapy current may extend through the blade 30 (preferably in a monopolar mode where the power extends to a remote return pad (not shown)) when the first activation button 62 or the second activation button 64 are pressed.

Figure 3A:
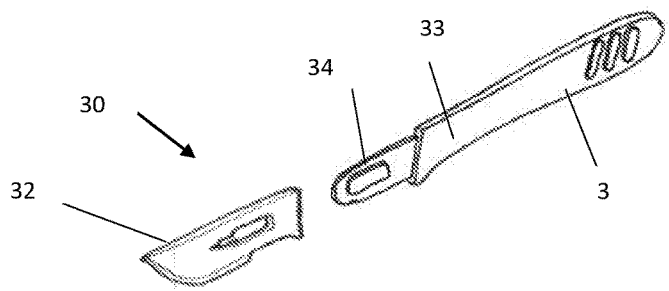
FIG. 3A illustrates a scalpel.

FIG. 3A illustrates a surgical instrument 3 that is a scalpel 30 with a blade 32 detached from the blade receptacle in a handle 33.

Figure 3B:
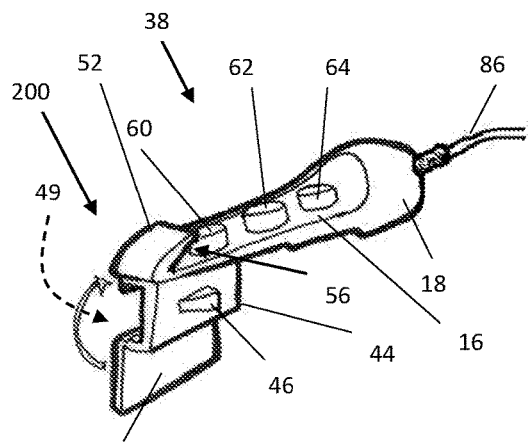
FIG. 3B illustrates a first portion with an enclosure for receiving a scalpel.

FIG. 3B illustrates a first portion 38. The first portion 38 includes a body 18 with a power cord 86, forward activation button 60, a first activation button 62, and a second activation button 64. A distal end 200 of the body 18 includes a tab 52 with a track 16 and a locking part 56. A body portion 44 is connected below the tab 52. The body portion 44 includes locking devices 46 and a flap 48. The flap 48 is movable between an open position (as shown) and a closed position (not shown) by moving in the direction of the arrow. When the flap 48 is moved to the closed position an enclosure 49 is formed that removably holds a scalpel (not shown).

Figure 3C:
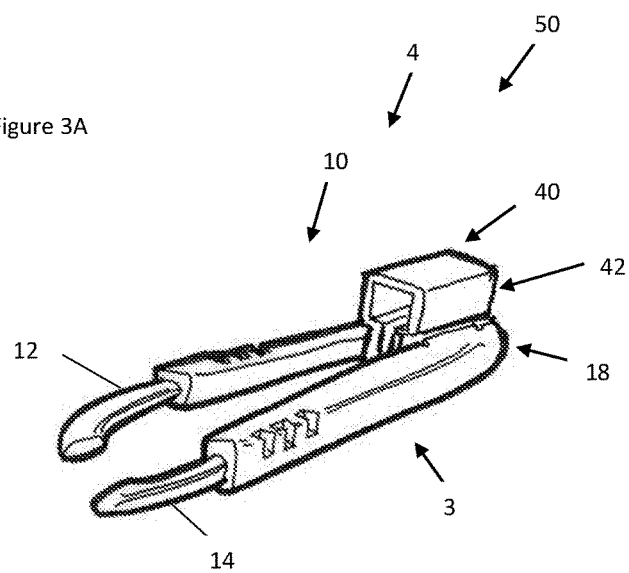
FIG. 3C illustrates a second portion including forceps.

FIG. 3C illustrates a second portion 50 which is a surgical instrument 3 that is configured as a forceps portion 4. The forceps portion 4 forms forceps 10 including a body 18 that connects a first working arm 12 and a second working arm 14. The body 18 includes a connection adapter 40 that is an interface portion 42. The interface portion 42 is a channel that is generally "T" shaped so that the tab and body portion of the first portion (not shown) extend through the channel to connect the first portion to the second portion 50.

Figure 3D:
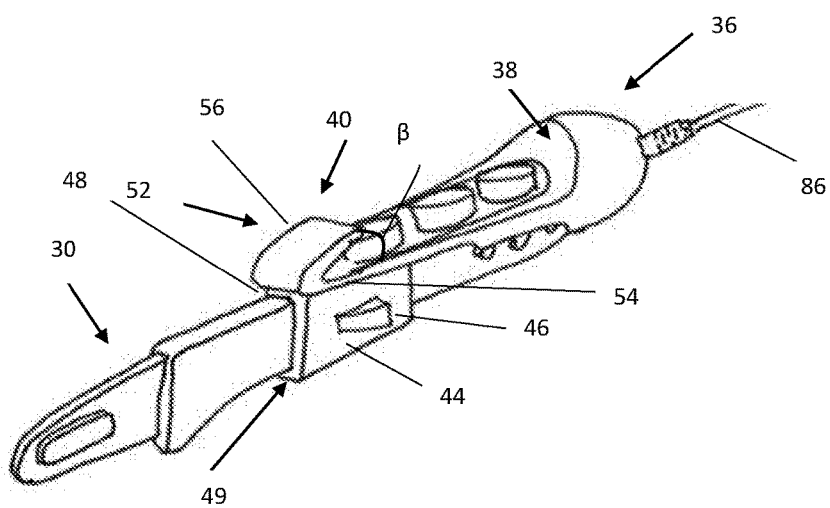
FIG. 3D illustrates the scalpel of FIG. 3B in a first portion of an interface.

FIG. 3D illustrates the scalpel 30 of FIG. 3A connected to a first portion 38 of FIG. 3B. The first portion 38 of an interface 36 includes a power cord 86 and a connection adapter 40 that is configured to connect the first portion 38 to a second portion (not shown). The connection adapter 40 as shown is a tab 52 that forms a connection with a second portion (not shown). The tab 52 includes a main part 54 and a locking part 56 that are separated by an angle (β). The first portion 38 includes a body portion 44 with locking devices 46 extending therefrom. The scalpel 30 extends into the body portion 44 and the flap 48 is closed so that the scalpel 30 is located within an enclosure 49.

Figure 3E:
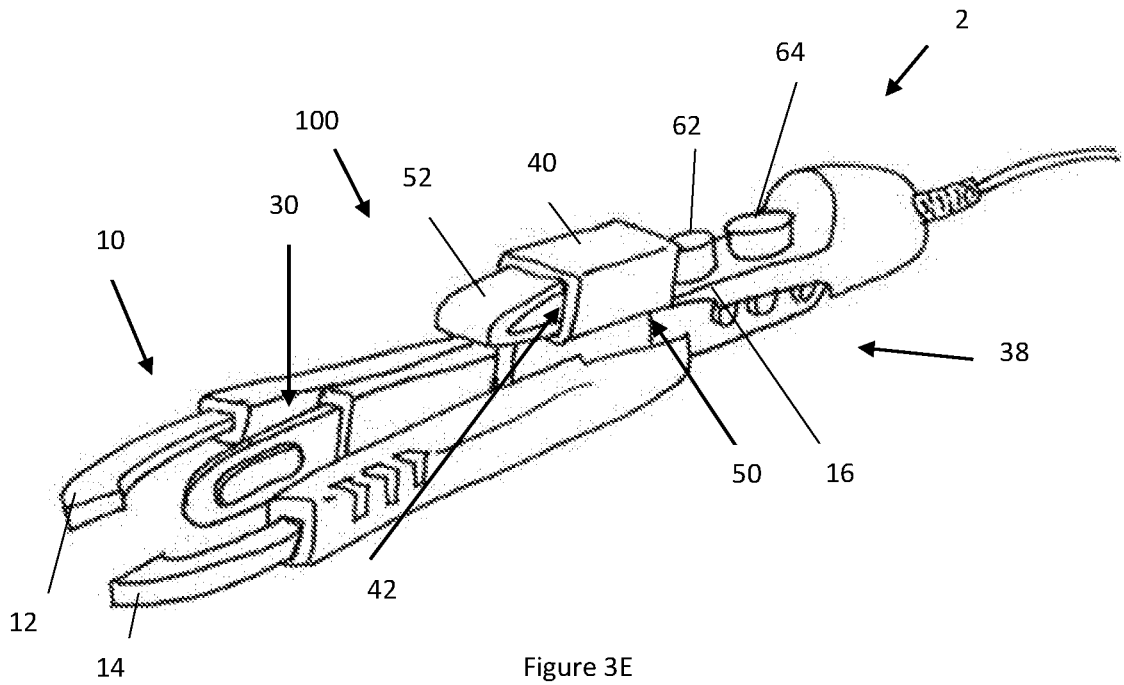
FIG. 3E illustrates the first portion and scalpel of FIG. 3D incorporated into the second portion of FIG. 3C with the forceps in the open position.

FIG. 3E illustrates a medical device 2 with a second portion 50 of FIG. 3C connected to the first portion 38 and scalpel 30 and first portion 38 of FIG. 3D. The second portion 50 includes forceps 10 with a first working arm 12 and a second working arm 14 extending therefrom with the blade 30 extending between the first working arm 12 and the second working arm 14. The second portion 50 has connection adapter 40 with an interface portion 42 that is a channel which receives the tab 52 and the body portion 44 of the first portion 38 so that the interface portion 42 slides along a track 16 of the tab 52. The connection adapter 40 as shown is in the distal position 100 so that the forceps 10 are extended beyond the scalpel 30 and the first activation button 62 and the second activation button 64 are exposed and can be actuated to provide a therapy current to the first working arm 12, the second working arm 14, or both.

Figure 3F:
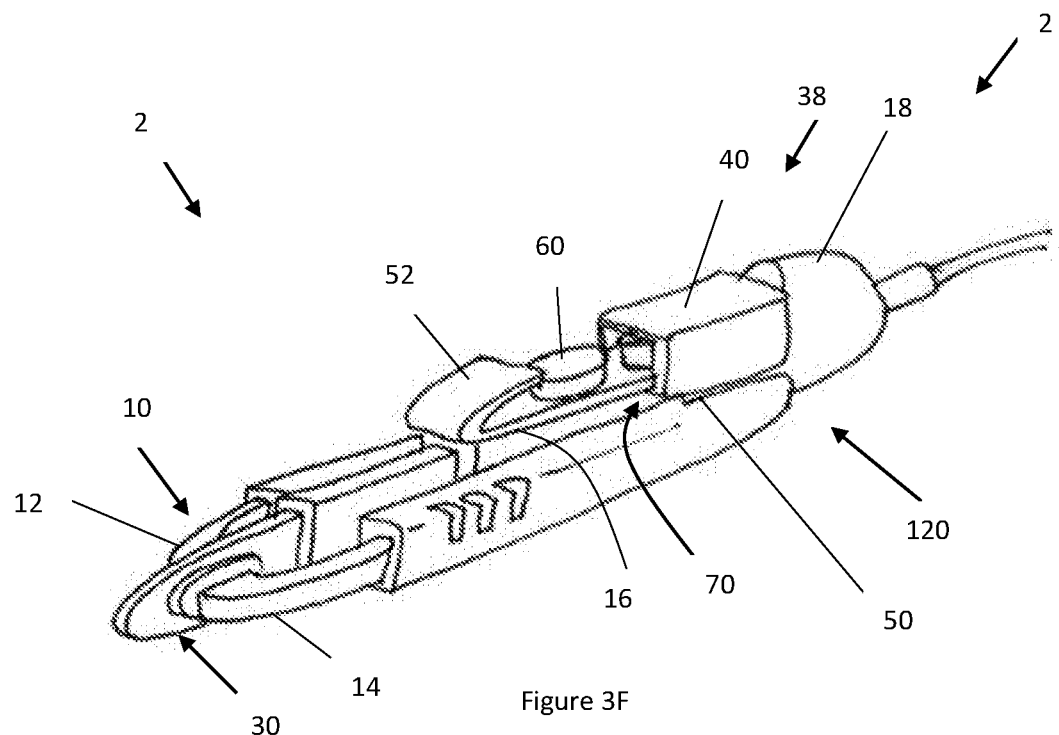
FIG. 3F illustrates the first portion and scalpel of FIG. 3D incorporated into the second portion of FIG. 3C with the forceps in the closed position.

FIG. 3F illustrates the medical device 2 of FIG. 3E with the connection adapter 40 moved to the proximal position 120 so that the forward activation button 60 is exposed and the forceps 10 are located proximal of the body 18 of the first portion 38 (i.e., the blade is extending beyond the ends of the forceps 10). As shown, the connection adapter 40 of the second portion 50 is slid to a proximal position 120 along a track 16 of the tab 52. The connection adapter 40 includes a groove 70 on the inside of the interface portion 42 and the groove 70 receives the track 54 so that the connection adapter 40 is movable along the track 54. The forceps 10 are in contact with the scalpel 30 and the forceps 10 are immobilized so that the forceps 10 cannot be used while the scalpel 30 is extended. The forceps 10 are connected to the connection adapter 40 so that as the connection adapter 40 is moved the forceps 10 move. In FIG. 3E the first working arm 12 and the second working arm 14 are in a distal position beyond the scalpel 30 and in FIG. 3F the first working arm 12 and the second working arm 14 are moved to a proximal position so that the scalpel 30 extends beyond the working arms 12, 14. The forward activation button 60 when pressed sends a therapy current through the scalpel 30.

Figure 4A:
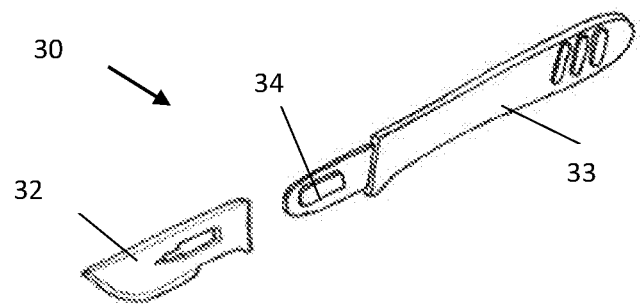
FIG. 4A illustrates a scalpel.

FIG. 4A illustrates a scalpel 30 with a blade 32 detached from the blade receptacle in a handle 33.

Figure 4B:
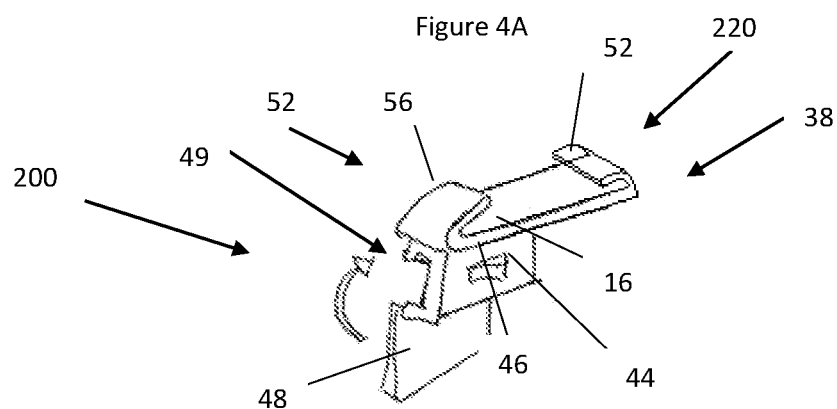
FIG. 4B illustrates a first portion.

FIG. 4B illustrates a first portion 38. The first portion 38 includes a tab 52 at a distal end 200 and a tab 52 at a proximal end 220 and including a track 16 between the tabs. The tab 52 as shown includes a locking part 56. A body portion 44 is connected below the tab 52 and track 16. The body portion 44 includes locking devices 46 and a flap 48. The flap 48 is movable between an open position (as shown) and a closed position (not shown). When the flap 48 is moved to the closed position an enclosure 49 is formed that removably holds a scalpel (not shown). The first portion 38 is free of power and activation buttons.

Figure 4C:
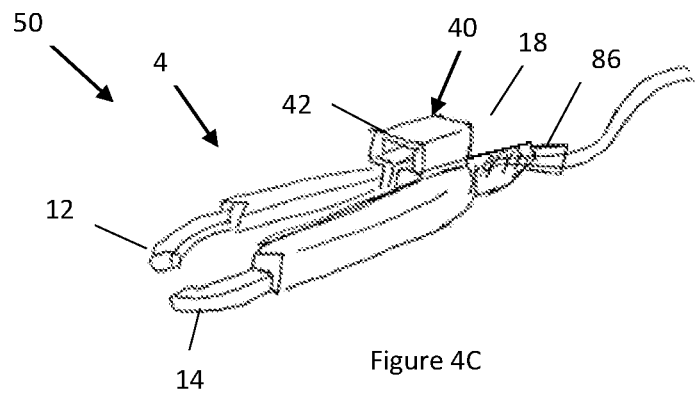
FIG. 4C illustrates a second portion.

FIG. 4C illustrates a second portion 50 with a forceps portion 4. The forceps portion 4 forms forceps 10 that include a body 18 that connects a first working arm 12 and a second working arm 14. The body 18 includes a power cord 86 and a connection adapter 40 that is an interface portion 42. The interface portion 42 is a channel that is generally "T" shaped so that the tab and body portion of the first portion (not shown) extend through the channel to connect the first portion to the second portion 50.

Figure 4D:
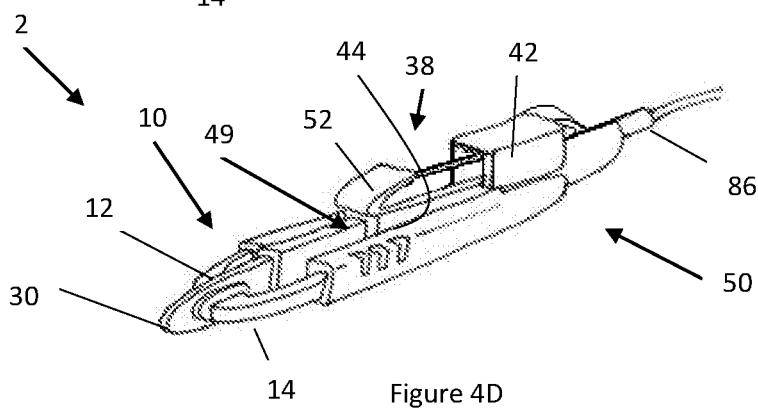
FIG. 4D illustrates the scalpel of FIG. 4A incorporated into the first portion of FIG. 4B and then attached to the second portion of FIG. 4C.

FIG. 4D illustrates a scalpel 30 of FIG. 4A connected within an enclosure 49 of the first portion 38 of FIG. 4B. The first portion 38 is connected to the second portion 50 of FIG. 4C by tab 52 and body portion 44 extending through the interface portion 42 forming an interface 36 so that a medical device 2 is formed. One of the tabs 52 extends through the interface portion 42 to connect the first portion 38 to the second first portion 50. The interface 36 creates a medical device 2 with forceps 10 and a scalpel 30. A therapy current extends into the medical device 10 through the power cord 86 and is activated by switches located off of the medical device 2 such as a foot petal or switches on a generator (not shown). The first working arm 12 and the second working arm 14 are in contact with the blade 30 so that the blade 30 is immobilized distal of the first working arm 12 and the second working arm 14.

Figure 5A:
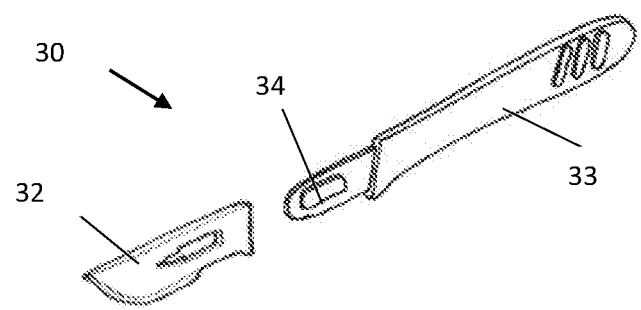
FIG. 5A illustrates a scalpel.

FIG. 5A illustrates a scalpel 30 with a blade 32 detached from the blade receptacle in a handle 33.

Figure 5B:
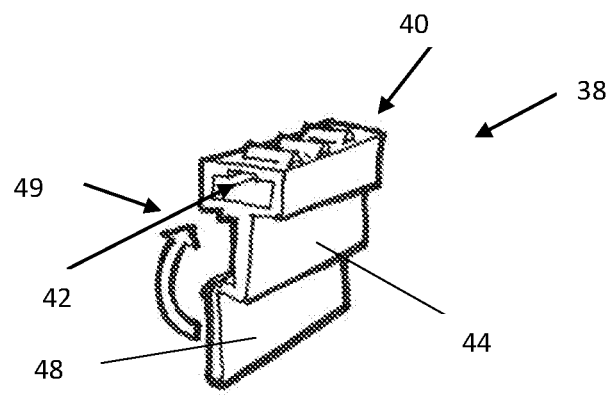
FIG. 5B illustrates a first portion.

FIG. 5B illustrates a first portion 38. The first portion 38 includes a body portion 44 with a flap 48 that when open (as shown receives a scalpel) and when closed forms an enclosure 49. A connection adapter 40 is located above the body portion 44. The connection adapter 40 includes an interface portion 42 that connects the first portion 38 to a second portion (not shown).

Figure 5C:
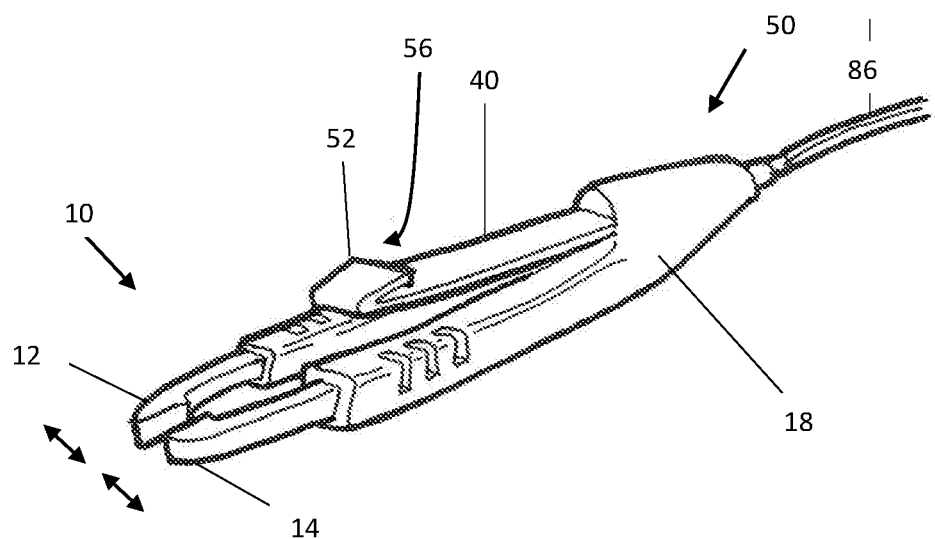
FIG. 5C illustrates a second portion including power.

FIG. 5C illustrates a perspective view of a second portion 50. The second portion 50 is forceps 10 with a connection adapter 40. The forceps 10 have a first working arm 12 and a second working arm 14, which are connected together at a body 18 and the first arm 12 and the second arm 14 pivot about the body 18 and are movable towards and away from each other as indicated by the arrows to create a gripping force. The body 18 receives a power cord 86 so that power extends into the forceps 10 and options through the first working arm 12, the second working arm 14, or both. A connection adapter 40 extends from the body 18. The connection adapter 40 includes a tab 52 that forms a locking part 56 so that a first portion (not shown) is movably locked to the second part 50.

Figure 5D:
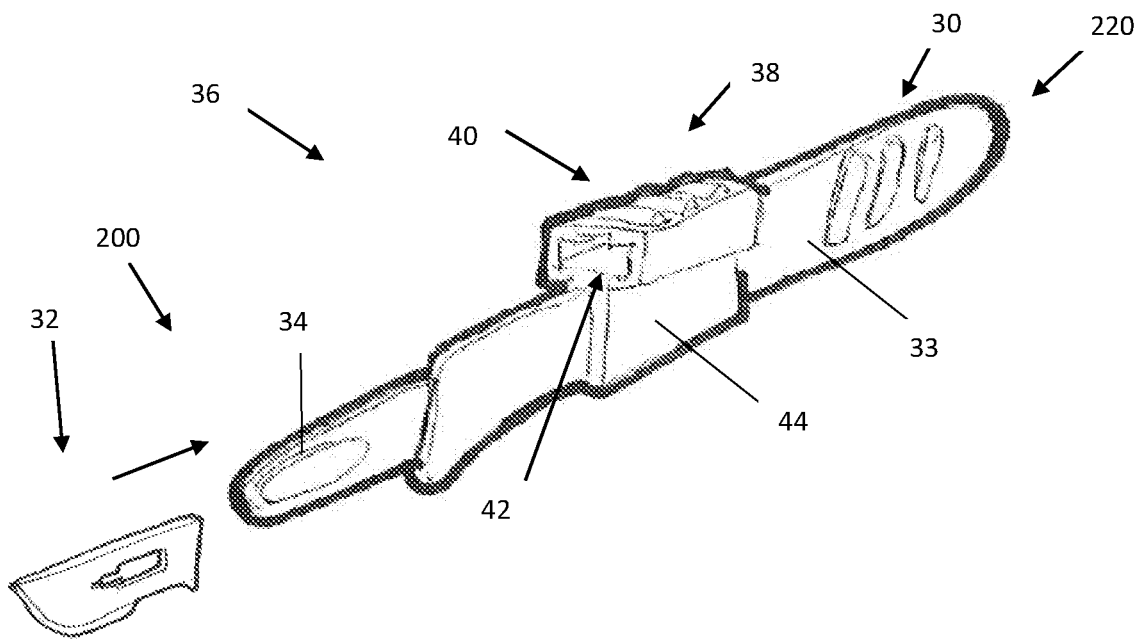
FIG. 5D illustrates the scalpel of FIG. 5A incorporated into the first portion of FIG. 5B.

FIG. 5D illustrates a cold blade scalpel 30 having a blade 32 at a distal end 200 and a handle 33 extending from the blade 32 to a proximal end 220. The scalpel 30 is integrally connected to a first portion 38 of an interface 36 (the first portion of the interface 36 being shown in FIG. 5B). The cold blade scalpel 30 has a distal end 200 with a blade receptacle 34 that accepts blades 32 so that the blades 32 can be changed. As shown, a blade 32 is being added to the scalpel 30. The connection adapter 40 includes an interface portion 42 that as shown is a channel. The interface portion 42 is located above a body portion 44 that is connected to the handle 33 of the scalpel 30. As shown, the handle 33 extends into a body portion 44, and the handle 33 is molded within the body portion 44 so that the first portion 38 and the scalpel 30 are formed as a single piece so that the scalpel 30 is connected to the first portion 38.

Figure 5E:
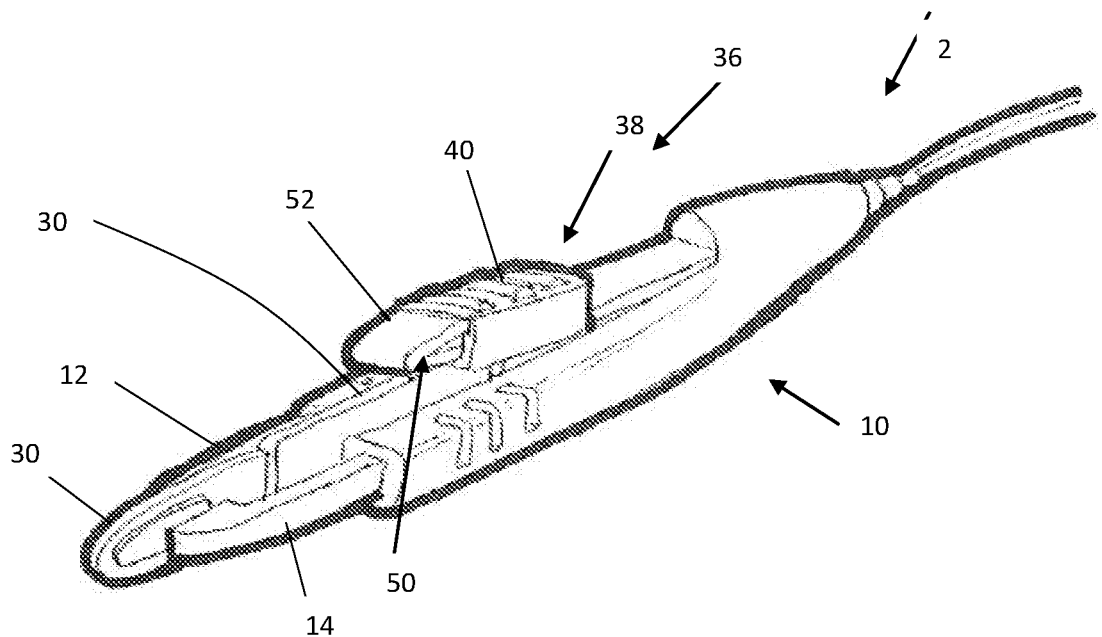
FIG. 5E illustrates the first portion of FIG. 5D connected to the second portion of FIG. 5C.

FIG. 5E illustrates a medical device 2 where the first portion 38 of FIGS. 5A and 5B (shown as FIG. 5D) are connected together and the second portion 50 of FIG. 5C are connected together forming an interface 36 so that the cold blade scalpel 30 is incorporated into forceps 10. As shown the interface 36 includes a first portion 38 connected to the scalpel 30 and a second portion 50 connected to the forceps 10. The first portion 38 has an interface portion 40 that receives a tab 52 of a second portion 50 so that the scalpel 30 and the forceps 10 are moveably connected together. The tab 52 extends through the interface portion 42 of the first portion 38 and then locks the scalpel 30 to the forceps 10 between the first working arm 12 and the second working arm 14. As shown, the medical device 2 is free of finger switches on the forceps 10, the scalpel 30, the first portion 38, and the second portion 50. The surgical device 2 is controlled by a foot petal (not shown) or switches on a generator (not shown).

Figure 6:
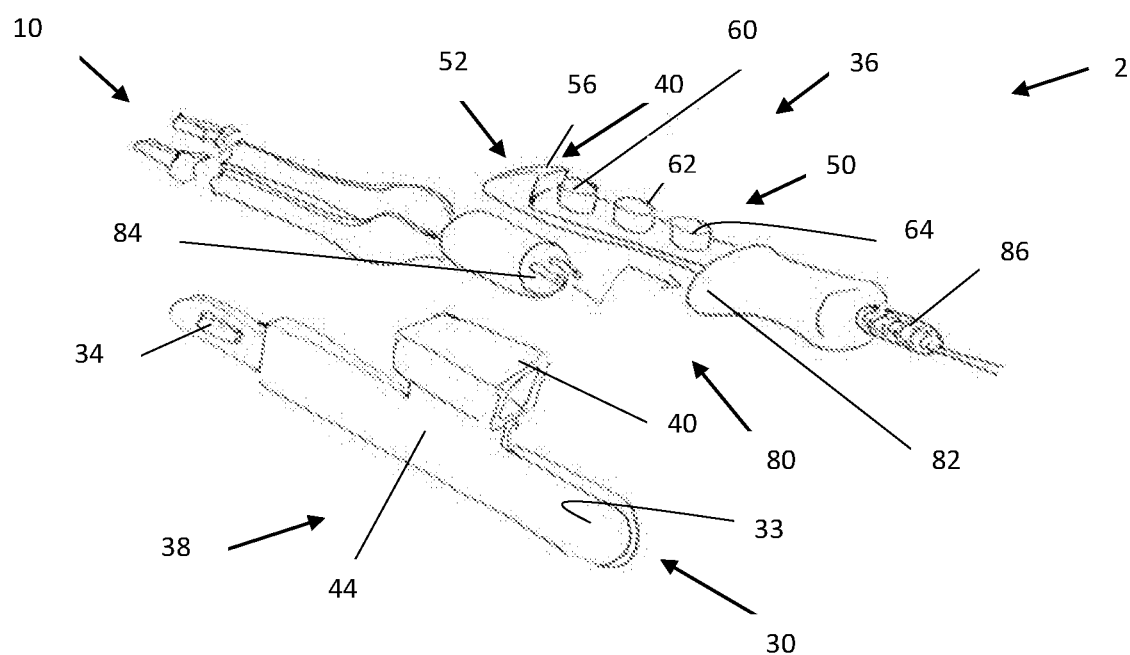
FIG. 6 illustrates an exploded view of a medical device.

FIG. 6 illustrates an exploded view of a medical device 2. As shown, the medical device 2 is in three parts that include forceps 10, a first portion 38, and second portion 50. The first portion 38 and the second portion 50 being part of an interface 36. The first portion 38 includes a scalpel 30 having a handle 33, a blade receptacle 34, a body portion 44, and a connection adapter 40. The connection adapter 40 of the first portion 38 is a channel that receives a connection adapter 40 of the second portion 50 which is a tab 52 that includes a locking part 56. Once connected the first portion 38 moves along the second portion 50 but the locking part 56 maintains a fixed connection. The second portion 50 includes a forward activation button 60, a first activation button 62 and a second activation button 64, and as the first portion 38 moves along the second portion 50 one or more of the buttons may become covered or uncovered. The second portion 50 includes a power cord 86 that supplies power to the plug receptor 82 that when the plug connector 84 of the forceps 10 is plugged in power is supplied through the port 80 to the forceps 10. Once use of the medical device 2 is complete the forceps and scalpel can be removed and the second portion 50 reused or discarded.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Medical device
3 Surgical instrument
4 Forceps portion
10 Forceps
12 First working arm
14 Second working arm
16 Track
18 Body
30 Scalpel
32 Blade
33 Handle
34 Blade receptacle
36 Interface
38 First Portion
40 Connection Adapter
42 Interface portion
44 Body portion
46 Locking Device
48 Flap
49 Enclosure
50 Second Portion
52 Tab
54 Main part
56 Locking part
60 Forward activation button
62 First activation button
64 Second activation button
80 Port
82 Plug receptor
84 Plug connector
86 Power cord
100 Distal Position
120 Proximal Position
200 Distal end
220 Proximal end

We claim:
1. A medical device comprising:
  a. an interface including:
    i. a first portion including:
      1. a body portion connected to a handle of a scalpel; and
      2. a connection adapter connected to and extending from the body portion;
    ii. a second portion;
  wherein the connection adapter includes an interface portion that is a channel and the second portion includes an interface portion that is a tab that extends into the channel so that the first portion is connected to the second portion;
  wherein the channel is longitudinally movable relative to the tab;
  wherein the tab is unidirectional so that the first portion is connected to the second portion in a first direction and prevented from being removed in a second opposing direction;
  wherein the first portion is movable between a distal position and a proximal position relative to the second portion;
  wherein the connection adapter covers one or more buttons in the distal position, the proximal position, or both; and
  wherein the first portion exposes one or more buttons in the distal position, the proximal position, or both.

2. The medical device of claim 1, wherein the second portion is connectable and removable from the first portion, a surgical instrument, or both.

3. The medical device of claim 1, wherein a surgical instrument is an integral part of the second portion.

4. The medical device of claim 1, wherein the interface is configured to connect to any scalpel.

5. The medical device of claim 1, wherein the second portion includes forceps.

6. The medical device of claim 1, wherein the second portion includes a port for receiving a surgical device, and the port includes a plug receptor or a plug connector that provides power from the second portion to the medical device.

7. The medical device of claim 6, wherein the surgical device is forceps that include a first working arm and a second working arm that are connected together at a body.

8. The medical device of claim 7, wherein the scalpel extends between the first working arm and the second working arm and is longitudinally movable relative to the first working arm and the second working arm.

9. The medical device of claim 7, wherein the first working arm and the second working arm lock the scalpel in place when the first portion is moved into a distal position.

10. The medical device of claim 1, wherein the scalpel is a cold blade scalpel.

11. The medical device of claim 1, wherein the body portion includes a locking device, and a first working arm connects to the locking device on a first side of the body portion and a second working arm connects to the locking device on a second side of the body portion.

12. The medical device of claim 1, wherein the first portion includes the scalpel and the second portion includes forceps, and the scalpel is movable longitudinally along a length of the forceps.

13. The medical device of claim 1, wherein the tab is spring loaded.

14. The medical device of claim 1, wherein the tab is a barbed tab.

15. The medical device of claim 1, wherein the tab includes one or more plastically deformable portions.

16. The medical device of claim 1, wherein the tab includes one or more elastically deformable portions.

17. A medical device comprising:
a. an interface including:
  i. a first portion including:
    1. a body portion connected to a handle of a scalpel; and
    2. a connection adapter connected to and extending from the body portion; and
  ii. a second portion;
wherein the connection adapter includes an interface portion that is a channel and the second portion includes an interface portion that is a tab that extends into the channel so that the first portion is connected to the second portion;
wherein the tab is spring loaded, includes one or more elastically deformable portions, or both;
wherein the channel is longitudinally movable relative to the tab; and
wherein the second portion is connectable and removable from the first portion, a surgical instrument, or both.

18. The medical device of claim 17, wherein the first portion is movable between a distal position and a proximal position relative to the second portion; the connection adapter covers one or more buttons in the distal position, the proximal position, or both; and the first portion exposes one or more buttons in the distal position, the proximal position, or both.

19. A medical device comprising:
a. an interface including:
  i. a first portion including:
    1. a body portion connected to a handle of a scalpel; and
    2. a connection adapter connected to and extending from the body portion; and
  ii. a second portion;
wherein the second portion includes an interface portion that is a channel and the connection adapter includes an interface portion that is a tab that extends into the channel so that the first portion is connected to the second portion; and
wherein the first portion is movable between a distal position and a proximal position relative to the second portion; the connection adapter covers one or more buttons in the distal position, the proximal position, or both; and the first portion exposes one or more buttons in the distal position, the proximal position, or both.

* * * * *